United States Patent

Suslavich

[11] Patent Number: 5,686,650
[45] Date of Patent: Nov. 11, 1997

[54] APPARATUS AND METHOD FOR CALIBRATING PARTICLE COUNTERS

[76] Inventor: Robert V. Suslavich, P.O. Box 2432, Woburn, Mass. 01888

[21] Appl. No.: 683,169
[22] Filed: Jul. 18, 1996
[51] Int. Cl.⁶ .................................................. G01N 15/02
[52] U.S. Cl. .................................................. 73/1 R
[58] Field of Search .................. 73/1 R, 1 G, 865.5, 73/3

[56] References Cited

U.S. PATENT DOCUMENTS

| | | | |
|---|---|---|---|
| 3,654,551 | 4/1972 | Flinchbaugh | 73/864.15 |
| 4,434,647 | 3/1984 | Whitcomb et al. | 73/1 R |
| 5,407,269 | 4/1995 | Sherry et al. | 73/1 R |
| 5,456,102 | 10/1995 | Moorehead | 73/1 G |

*Primary Examiner*—Hezron E. Williams
*Assistant Examiner*—Nashmiya Ashraf
*Attorney, Agent, or Firm*—Joseph E. Funk; Hamblett & Kerrigan PA

[57] ABSTRACT

Apparatus is disclosed for dispensing a standardized test fluid used for calibrating a counter while preventing the formation of bubbles in the test fluid and preventing the introduction of extraneous air born particulate contamination, both of which detrimentally affect the calibration. The test fluid is contained in a semi-rigid, ventless container that is partially filled with the test fluid and partially filled with a gas. The container is held in an inverted position by a spring clip attached to the apparatus. The spring clip applies external pressure to the container, partially collapsing same, and thereby pressurizing the gas inside the container above ambient air pressure. A peristaltic pump withdraws the test fluid from the container and precisely meters it through an injection valve and a three way valve to the particle counter. As the fluid is withdrawn the container further collapses to maintain pressurization of the gas. The continued pressurization of the gas allows the pump to precisely dispense the test fluid until the entire contents of the ventless container are dispensed, and at the same time eliminates the formation of a partial vacuum in the container to thereby prevent the formation of bubbles in the test fluid as it is withdrawn from the container.

7 Claims, 1 Drawing Sheet

APPARATUS AND METHOD FOR CALIBRATING PARTICLE COUNTERS

BACKGROUND OF THE INVENTION

This invention relates in general to apparatus and a method for calibrating particle counters by introducing a test fluid having known particle size and concentration level into a flow of fluid having an established purity level to a particle counter to thereby provide a testing standard for calibrating the particle counter. This invention is designed to be used in conjunction with a particle counter manufacturer's calibration methods which include electrical adjustment, optical alignment, and optical surface cleaning within the particle counter. It also allows an end user of a particle counter to test the counter on site to verify the operation of the instrument and to assure that the instrument is sizing and counting particles correctly.

FIELD OF THE INVENTION

Accurate testing and calibration of particle counters used to measure particle levels or contaminant levels in flowing fluids requires the repeatable introduction of a test fluid having a standardized particle suspension into a particle counter being tested or calibrated. The standardized test fluid has in suspension in a carrier fluid, particles of a known size and concentration, and are free of other contamination of known or unknown source which will result in spurious responses from a particle counter under test or being calibrated. One standardized test fluid in the prior art has latex spheres of known size suspended in pure, de-ionized water in a known concentration. Preparation of the standardized test fluid requires great precision to assure accurate particle size and concentration, along with freedom from unwanted particle contamination. This is required so that particle counter calibrations are repeatable to assure accuracy of present and future calibrations.

In the prior art standardized test fluids are introduced to particle counters undergoing calibration or testing in a variety of ways. Gravity feed, pumped injection, and vacuum aspiration are those methods generally in use.

When gravity feed is used to introduce a standardized test fluid to a particle counter the container of standardized test fluid must be mounted high enough above the particle counter being tested or calibrated to overcome flow resistance and water pressure in the connecting piping and in the particle counter. This is physically awkward and when the person testing the system wants to switch from a standardized test fluid to a baseline fluid, such as pure de-ionized water, there is a relatively long delay as the remaining standardized test fluid flows through the relatively long connecting piping. This long delay also occurs when switching from the de-ionized water to the standardized test fluid.

Utilizing a pump between the container with the standardized test fluid and the input of the particle counter being tested or calibrated does not eliminate all the problems of gravity feed arrangements, and it creates another problem. As test fluid is pumped out of its sealed container a negative pressure is created in the container which causes bubbles to be formed in the test fluid from dissolved gasses in the test fluid. The particle counter counts these bubbles along with the latex spheres which results in an erroneous measurement. The result is a wrong calibration.

Locating the pump at the output of the particle counter does not eliminate the low pressure inside the container with the standardized test fluid and bubbles are still created which results in erroneous readings by the particle counter. In fact, by drawing the test fluid and de-ionized water through the particle counter, pressure drops occurring inside the particle counter optical cell exacerbates the degassing (bubble formation) phenomenon.

Another method of introducing a standardized test fluid into a particle counter is to inject it via a syringe into a flow of pure, de-ionized water that is input to the particle counter. This technique introduces other problems. The syringe needle must puncture a membrane which can result in unwanted particles being broken off the membrane and contaminating the fluid flowing into the particle counter being tested or calibrated. This produces an erroneous result. In addition, hypodermic syringes are Food and Drug Administration (FDA) controlled medical devices. Permits, locked storage areas, and personnel training and control are all required impediments to the use of these devices in industrial facilities are further, used syringes must be destroyed and disposed of according to law.

Pumped injection of standardized test fluids is known in the art and one such arrangement is taught and claimed in U.S. Pat. No. 5,407,269.

Thus, there is a need in the art for apparatus and a method for introducing a standardized test fluid into a particle counter which is being tested or calibrated at a precise flow rate, without having any air bubbles created or extraneous air born particulate contamination introduced that detrimentally affect the testing or calibration.

DESCRIPTION OF THE DRAWINGS

The present invention will be best understood when reading the following Detailed Description in conjunction with the drawing in which.

DETAILED DESCRIPTION

Figure 1:
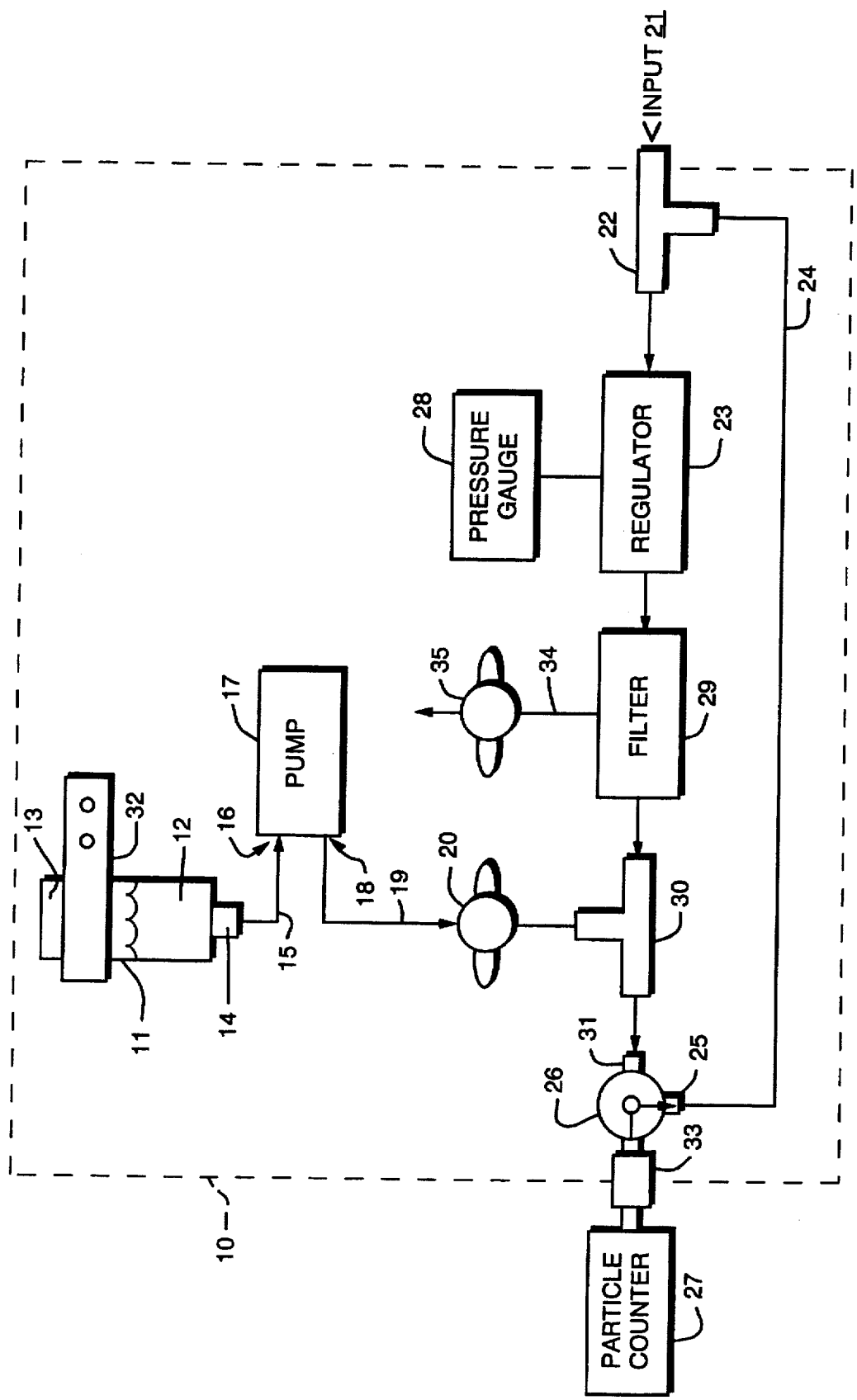
FIG. 1 shows a block diagram of my novel calibration apparatus for introducing a standardized test fluid into a flow of pure de-ionized water or other compatible fluid entering a particle counter which is being calibrated or tested.

In FIG. 1 is shown a block diagram of my novel apparatus 10 which is used for introducing a standardized test fluid into a flow of pure de-ionized water or other compatible fluid entering a particle counter which is being calibrated or tested. My novel apparatus easily mounts in a small case (shown in dotted line) for portability and ease of use. It may also be left connected to the input of a particle counter (not shown) while permitting easy switching of the test fluid (for calibration) and another fluid having particles or contamination that are to be counted. This is described in more detail further in this detailed specification.

As described in detail hereinafter, bubbles are prevented from forming in the standardized test fluid as it is input via other elements of my novel system to a particle counter to either test or calibrate the counter. Particle counters are well known in the art and are not discussed in any detail herein. Exemplary particle counters are taught and claimed in U.S. Pat. Nos. 5,245,318, 5,410,403, and 5,456,102. Standardized test fluids are also well known in the art and generally comprise a known size of latex spheres held in suspension in pure de-ionized water with a small amount of surfactant. In bulk solutions only an approximate concentration of latex particles is given. This approximation is derived from a bulk polymer concentration equation other measurements of the actual concentration of latex particles are provided by the manufacturers. The test fluid utilized with the novel apparatus described herein also has microbial inhibitors added to inhibit the growth of microbes in the test fluid. Unwanted microbes multiplying in the test fluid can be counted by the particle counter and thereby cause erroneous calibration readings.

My novel calibration apparatus 10 comprises a ventless semi-rigid plastic container 11 which is no more than one-half full of standardized test fluid 12. The remainder of the container is filled with a gas 13, which may be air, but may be other gasses as well. Container 11 has a standard Luer vial fitting 14 output to which is easily connected a piece of small diameter plastic tubing 15 with corresponding nuer fitting attached. Container 11 is held in an inverted position in the apparatus case as shown in FIG. 1 by a spring clip 32. In this position the test fluid 12 is adjacent the dropper fitting 14 and the gas 13 is above the test fluid 12.

Spring clip 32 not only holds container 11 in the inverted position but also applies pressure to the ventless, semi-rigid container 11, partially compressing it and thereby pressurizing gas 13 in container 11 to a pressure greater than the ambient air pressure around container 11.

Tubing 15 is connected to input 16 of a peristaltic pump 17, which is well known in the medical devices art so is not described in detail hereinafter. Pump 17 is used to pump test fluid 12 therethrough and via its output 18 and another piece of small diameter plastic tubing 19 to a stop cock valve 20. In the preferred embodiment of the invention tubing 15 is connected to both container 11 and input 16 of pump 17 via Luer connectors which are well known in the medical devices art. Luer connectors are also used to connect tubing 19 to output 18 of pump 17 and to stop cock valve 20. Luer valves 17 are also used for other connections throughout my novel apparatus, but those skilled in the art will realize that other connector means may be used while not departing from the teaching of my invention. Tubing 15 and 19 may either be separate pieces or one continuous piece of tubing passing through the pump rollers of peristaltic pump 17. It is preferred that the tubing be for a single use with each container 11 of standardized test fluid 12. The tubing is then discarded to minimize the possibility of cross contamination or excessive spalling of the flexible tubing inside pump 17. Excessive wear of the tubing in pump 17 will cause erroneous counts in particle counter 27.

For calibration and testing purposes a source of pure, de-ionized water or other compatible fluid (not shown) is input under pressure to my novel apparatus at input 21, and can pass through T-connector 22 to either a pressure regulator 23, or through plastic tubing 24 to the input 25 a multi-output valve 26. The operation of valve 26 is selected by the operator of calibration apparatus 10 and determines what fluid flow exits apparatus 10 to particle counter 27. The operation of valve 26 in controlling the functioning of apparatus 10 is described further in this specification.

Pressure regulator 23 is adjusted to regulate the pressure of the water output from regulator 23 to between ten and twenty psig (pounds per square inch gauge), and preferably to fifteen psig. Connected to one output of manually operated pressure regulator 23 is a pressure gauge 28 which measures the output pressure of regulator 23 and is used to adjust the pressure regulator 23 output to fifteen pounds psig.

The pressure regulated pure, de-ionized water or another compatible fluid (not shown) output from pressure regulator 23 is input to sub-micron filter 29. Filter 29 is well known in the art and filters any unwanted particles over 0.2 microns in size from the pure, de-ionized water. Other micron rated filters may be substituted without affecting the operation of the apparatus.

The filtered water output from filter 29 is applied to one of the inputs of T-connector 30. Mother input of T-connector 30 is connected to stop cock valve 20, and the third input of T-connector 30 is connected to input 31 of a three-way valve 26 of which each fluid connection is utilized but only two of the three valve stem positions are accessible. As shown in FIG. 1, output port 33 is common and is connected to either output port 25 or 31 by rotating a handle (not shown) on valve 26 ninety degrees between ports 25 and 31. As shown in FIG. 1, common output port 33 is connected to port 25 so de-ionized water at input 21 will flow through tubing 24 and valve 26 to particle counter 27. The output 33 of valve 26 is connected to particle counter 27. Valve 26 is manually operated to connect either the un-filtered de-ionized water in tubing 24 via output 33 to particle counter 27, or the filtered de-ionized water at input 31 (with or without standardized test fluid) to particle counter 27.

Finally, connected to an output 34 of filter 29 is another stop cock valve 35. Valve 35 is physically oriented to be above filter 29. The purpose of valve 35 is to bleed air from filter 29 when my novel apparatus 10 is first set up to be used. Valve 35 is opened while pure, de-ionized water or another compatible fluid is input to filter 29 from pressure regulator 23. The fluid flows through pressure regulator 23 and filter 29 and out open valve 35 to remove any air in the system that had been in regulator 23 and filter 29, and which may introduce air bubbles into the water or other fluid flow through apparatus 10. Any air bubbles detrimentally affect the testing, calibration or general operation of particle counter 27.

In operation calibration apparatus is initially connected between a source of de-ionized water or another compatible fluid, under pressure, and particle counter 27 and shown in FIG. 1 and described hereinabove. Initially there is air in the system that must be removed. Valve 20 is placed in its closed position, and valve 26 is set so that un-filtered, de-ionized water in tubing 24 will pass through valve 26 to particle counter 27. The flow of water is initially through tubing 24 and particle counter 27 to remove air from counter 27. In addition, a base line particle measurement can be made using particle counter 27.

The next step is to set valve 26 so that de-ionized water or another compatible fluid passing through sub-micron filter 29 will pass through valve 26 to particle counter 27, and air bleed valve 35 is opened. By setting valve 26 in this position no water will flow through tubing 24. Air in pressure regulator 23 and filter 29 will be bled off via open stop cock valve 35. Valve 35 is then closed and filtered, de-ionized water or other compatible fluid flows through particle counter 27. Initially, any remaining air in the system will be flushed out as the filtered, de-ionized water or other compatible fluid flows through apparatus 10 and particle counter 27. When particle counter 27 stabilizes all air is removed and particle counter 27 is ready to be calibrated.

A semi-rigid container 11 of standardized test fluid 12 is mounted in apparatus 10 in an inverted fashion under spring clip 32. Container 11 has a standard Luer vial fitting 14 output to which is easily connected plastic tubing 15 using a mating Luer connector. Container 11 may be mounted before or after air is bled out of the system as described above. However, container 11 may not be mounted under spring clamp 32 until tubing 15 and 19 is installed in peristaltic pump 17 and connected to valve 20.

As previously described, container 11 is preferably no more than half full of standardized test fluid 12 and the remainder is a gas 13 which may be air. By being mounted in an inverted fashion gas 13 is above test fluid 12. Spring clip 32 not only holds container 11 in the inverted position but also places sufficient pressure on the wall of container 11 so that it is partially collapsed and thereby pressurizes gas 13 inside. The pressure on gas 13 is greater than the ambient air pressure around apparatus 10. Because gas 13 is kept pressurized as test fluid 12 is withdrawn from container 11 by pump 17, no vacuum is ever created in container 11. Thus, no air bubbles are created in test fluid 12 which will cause erroneous calibration readings in particle counter 27. Also, since container 11 is ventless, the introduction of unwanted particles from the ambient air into the test fluid 12 is minimized as test fluid 12 is withdrawn from container 11 with pump 17. The delivery accuracy and precision of pump 17 is improved and maintained as fluid is withdrawn from container 11 since pump 17 does not have to overcome a changing partial vacuum in container 11 as fluid 12 is withdrawn therefrom.

After filtered, pure, de-ionized water is passed through regulator 23, filter 29, valve 26 and particle detector, peristaltic pump 17 is turned on and valve 20 is opened. The standardized test fluid 12, which is under pressure due to spring clip 32 and gas 13, flows into T-connector 30 where it mixes with the filtered, de-ionized water and the mixture then flows through valve 26 and particle counter 27. In the first moments of this flow some air may be present from tubing 15 and 19. Thereafter, only the filtered, de-ionized water or other compatible fluid and test fluid 12 mixture flows through particle counter 27, with no air bubbles, and particle counter 27 may be accurately calibrated because it will only measure the particle size and concentration of standardized test fluid 12.

While what has been described herein is the preferred embodiment of the invention it will be understood by those skilled in the art that numerous changes may be made without departing from the spirit and scope of the invention. For example, while the test fluid described herein is latex spheres in a de-ionized water carrier, other standardized test fluids and particulates and micro-organisms may be utilized. Further, other means may be utilized for pressurizing and maintaining pressurization of the air in the container of standardized test fluid as the test fluid flows from the container.

What is claimed is:

1. Apparatus for introducing a standardized test fluid via a pump into a particle counter to test and calibrate the counter, said test fluid having a known concentration of a known size of particles mixed in a pure liquid, said apparatus comprising:

a container made of a semi-rigid material and containing said standardized test fluid, said standardized test fluid output being withdrawn from said container and input to said particle counter to test and calibrate said counter;

wherein said container is only partially filled with said standardized test fluid and the remainder of said container is filled with a gas, and said test fluid is withdrawn from said container using said pump for precise delivery to said particle counter; and means for pressurizing said gas inside said container above ambient air pressure external to said container and thereby preventing the formation of bubbles in said test fluid as said test fluid is withdrawn from said container, said means for pressurizing applying pressure to the external surface of said container and thereby causing said container to collapse as said test fluid is withdrawn from said container and thereby maintain the pressurization of said gas inside said container.

2. The apparatus in accordance with claim 1 wherein said means for applying pressure to the external surface of said container comprises a spring clip that is used to hold said container in an inverted position while maintaining the pressurization of said gas.

3. The apparatus in accordance with claim 2 wherein said test fluid comprises pure, de-ionized water in which is suspended a known concentration of a known size of latex spheres.

4. The apparatus in accordance with claim 3 wherein said test fluid further comprises:

microbial inhibitors to inhibit the growth of microbes in said test fluid; and a suspension agent which causes said latex spheres to remain in suspension in said test fluid.

5. A method of preventing the formation of gas bubbles in a container of standardized test fluid, which fluid is withdrawn from said container using a pump and used to test and calibrate a particle counter, the method comprising the steps of:

connecting said container partially filled with said test fluid and partially filled with a gas to said pump to dispense said test fluid to said particle counter; and applying pressure to the external surface of said container to pressurize said gas inside by collapsing said container which is made of a semi-rigid material, said pressurized gas eliminating the formation of a partial vacuum in said container and thereby preventing the formation of bubbles in said test fluid as said test fluid is withdrawn from said container by said pump for delivery to said particle counter.

6. The method in accordance with claim 5 further comprising the step of pre-pressurizing said gas inside said container before said container is used, and applying said pressure to the external surface of said container to maintain the pressurization of said gas inside said container as said container collapses when said test fluid is withdrawn therefrom.

7. Apparatus for introducing a standardized test fluid from a partially filled, semi-rigid container to a particle counter to test and calibrate the counter, the test fluid having a known concentration of a known size of particles mixed in a pure liquid, said apparatus comprising:

means for pressurizing said container and maintaining the pressurization in said container as said test fluid is withdrawn from said container, said means for pressurizing applying pressure to the external surface of said container and thereby causing said container to collapse as said test fluid is withdrawn from said container and thereby maintain the pressurization of said gas inside said container, said pressurization preventing a vacuum from being created in said container as test fluid is withdrawn from said container which prevents air bubbles from being created in said test fluid that will cause erroneous calibration readings in said particle counter, and said pressurized container preventing airborne particles from entering said container that will also cause erroneous calibration readings in said particle counter.

* * * * *